(12) United States Patent
Bertan et al.

(10) Patent No.: US 6,461,348 B1
(45) Date of Patent: Oct. 8, 2002

(54) PHOTO-THERMAL EPILATION APPARATUS WITH ADVANCED ENERGY STORAGE ARRANGEMENT

(76) Inventors: Howard S. Bertan, 41 Moss La., Jericho, NY (US) 11753; Kenneth L. Short, 142 Quaker Path, Setauket, NY (US) 11733

(*) Notice: Subject to any disclaimer, the term of this patent is extended or adjusted under 35 U.S.C. 154(b) by 0 days.

(21) Appl. No.: 09/384,122

(22) Filed: Aug. 27, 1999

(51) Int. Cl.[7] ............................................. A61B 18/18
(52) U.S. Cl. ................... 606/9; 315/200 A; 315/214; 315/241 R; 315/244
(58) Field of Search .................. 606/9–13; 315/204 R, 315/214, 224, 227 R, 241 R, 244, 200 A; 607/88

(56) References Cited

U.S. PATENT DOCUMENTS

| | | |
|---|---|---|
| 3,693,623 A | 9/1972 | Harte et al. |
| 3,834,391 A | 9/1974 | Block |
| 4,388,924 A | 6/1983 | Weissman et al. |
| 4,617,926 A | 10/1986 | Sutton |
| 4,743,809 A | 5/1988 | Vlahos |
| 5,026,369 A | 6/1991 | Cole |
| 5,105,126 A | 4/1992 | Whitesel |
| 5,226,907 A | 7/1993 | Tankovich |
| 5,381,077 A | 1/1995 | McGuire |
| 5,425,728 A | 6/1995 | Tankovich |
| 5,595,568 A | 1/1997 | Anderson et al. |
| 5,735,844 A | 4/1998 | Anderson et al. |

*Primary Examiner*—David M. Shay
(74) *Attorney, Agent, or Firm*—Island Patent; F. S. Tierno (57) ABSTRACT

A photo-thermal epilation apparatus enables the efficient delivery of a high energy light pulse of a sufficiently short duration to a selected follicle to effect permanent hair removal. The apparatus includes a flash lamp powered by a power supply module having an energy storage module interposed between the power supply module and the flash lamp. The energy storage module, which has an output or network impedance matched to the flash lamp, produces a flattened and extended current pulse that is coupled from the energy storage module to the flash lamp in order to the energize the flash lamp to produce the desired high energy light pulse. An optical system, which includes a tapered needle-less probe, is included to receive the light pulse produced by the flash lamp and efficiently deliver the light pulse to a selected hair follicle to effect the photo-thermal epilation of the associated growth support tissue.

18 Claims, 8 Drawing Sheets

PHOTO-THERMAL EPILATION APPARATUS WITH ADVANCED ENERGY STORAGE ARRANGEMENT

BACKGROUND OF THE INVENTION

1. Field of the Invention

The present invention relates generally to systems that effect hair removal, also termed epilation or depilation. More particularly, the invention relates to apparatus that provide for permanent hair removal by photo-thermal depilation techniques.

2. Description of the Prior Art

Permanent hair removal can be realized by several known techniques, including electrolysis and photo-thermal depilation. Each of these methods involves the destruction of a nutrient providing area at the base of the follicle. This area, which may be termed the 'growth support tissue' of the follicle is the papilla, which is supplied with nutrients by capillary blood vessels. It is well known in the art that simply (physically) removing a hair will not prevent another from growing in its place. To achieve permanent hair removal the growth support tissue at the base of the follicle must be destroyed.

Traditional electrolysis employs a technique wherein a needle is inserted into the sub-dermal follicle region. The needle serves as an electrode from which an electric current emanates to coagulate and destroy the growth support tissue (of a selected follicle). However, traditional electrolysis is considered to have associated with it several undesirable characteristics. First, the actual effectiveness of electrolysis is greatly determined by the skill of the operator and the proper placement of the needle within the follicle. A person undergoing such a procedure will experience some discomfort, even when topical anesthetic lotions are applied. In addition, it is not uncommon for an individual to experience redness and possibly tenderness in a treated area for a period of time following a treatment session.

In situations where the operator's traditional electrolysis skill was marginal, permanent hair removal may not be efficiently realized, with follow up treatment sessions required to re-treat the same area. Finally, for individuals who have an aversion to needles and needle-based devices, this method of depilation can be quite unattractive.

A subsequent technique was developed that delivers energy to the base of the follicle by employing a high energy light pulse. Thus, photo-coagulation is accomplished by delivering pulsed light energy of a sufficient energy level, having a sufficiently short duration. If the (light) energy is delivered to the follicle over too long a period of time, a 'self-cooling' ability of the epidermis results in an incomplete photo-coagulation, and permanent hair removal may not result. This process is greatly preferred over traditional electrolysis, especially if-a needle-less probe is used to deliver the light pulse to the follicle. Also, when a light pulse is properly delivered to a selected follicle having a proper energy level, for a sufficiently short duration, painless, irritation free depilation results.

Previous photo-thermal depilation systems have proven that a high energy xenon flash lamp may be employed to produce a light energy pulse capable of causing photo-thermal coagulation at the base of the follicle. However, controlling and maintaining the light pulse intensity and or light pulse duration over an extended period of time has proven difficult, especially as the flash lamp ages. Other common problems involved providing a pulse of a sufficiently short duration, and efficiently delivering the light pulse to a selected follicle. In particular, prior art systems have not provided efficient and reliable arrangements to deliver a high energy light pulse produced by a flash lamp to a selected follicle to effect the desired photo-thermal depilation. As a result, such systems employed xenon flash lamps that produced light pulses having significantly greater energy levels than actually required (essentially due to their inefficient optical delivery structures and their simple and inefficient power supplying means).

Other known systems, such as that disclosed by the utility U.S. Pat. No. 3,693,623 to Harte et al., required a narrow and hollow needle-type probe having a diameter of 125 to 200 microns, which required the operator to insert the probe into the upper follicle region. As with traditional electrolysis, operator skill again becomes a critical consideration for such a system. Further, as discussed above, when a light pulse produced is of too long a (temporal) duration, epidermal self cooling results. In such cases, additional optical energy must be provided, to cause the desired photo-thermal depilation. This additional energy may also result in discomfort to the patience/client receiving the depilation treatment. Finally, known prior art systems do not provide any means to conveniently calibrate or set the intensity level of the high energy light pulse to a desired level. This type of self-calibration capability is most desirable to provide safe, consistent, and effective photo-depilation over a long period of time.

Therefore, there is a need to provide new and improved apparatus to provide reliable, safe, and consistent photo-thermal depilation to effect permanent hair removal. Embodiments of the present invention may be provided incorporating one or more of the following capabilities, features, characteristics, and or advantages:

an 'energy supplying arrangement' to deliver a shaped current pulse having an appropriate duration to energize a suitable flash lamp (e.g., a xenon flash lamp);

a charged delay line provided as a component of the energy supplying arrangement;

an optical light guide having a diameter of 2 to 4 millimeters into which a high energy light pulse is efficiently coupled from a suitable flash lamp;

a needle-less tapered probe having a simple construction that is provided at an output end of the optical light guide;

the tapered probe specifically structured to receive the light pulse and efficiently concentrate the light pulse to a diameter of approximately 0.5 milli-meters, for delivery to a selected hair follicle;

preferably delivers approximately 5 to 15 joules per square centimeter of energy that may be applied to the hair follicle at the epidermal level (no need to penetrate the skin with a needle-type probe);

a calibration portal to receive the output end of the tapered probe to enable an operator to calibrate the intensity (or energy) level of the light pulse delivered each time the flash lamp is triggered;

a control means (e.g., an embedded computer) to periodically trigger the flash lamp at a pre-determined rate, for a pre-determined length of time (i.e., session);

a user interface to enable a user or operator to establish at least one of the pre-determined rate and the pre-determined length of time for a respective session;

embodiments wherein an external computer is employed for collecting session and billing information, enabling remote monitoring of the photo-thermal epilation system's operation and usage, providing for the remote billing and or remote credit allocation, supporting remote maintenance monitoring, accumulating client data, assisting in performing operational analysis, providing intelligent operator guidance and assistance, performing operator training, monitoring, and evaluation, monitoring compliance with standard operational requirements, etc.; and generally economical and reliable construction using a number of proven off-the-shelf components.

The above listed items, capabilities, characteristics, features, and or associated novel features of the presently described invention, as well as others, will become clear from a careful review of the description and figures provided herein. Attention is called to the fact, however, that the drawings and descriptions included herewith are illustrative only. Variations are contemplated as being part of the invention, limited only by the scope of the appended claims.

SUMMARY OF THE INVENTION

In accordance with the invention, a photo-thermal epilation apparatus is provided that is employable to effect permanent hair removal. The desired-permanent hair removal is realized by delivering a high energy light pulse of a sufficiently short duration to effect photo-thermal coagulation of growth support tissue of a selected hair follicle. The apparatus includes a flash lamp having an energy input coupling and provisions for triggering. A power supply module is configured with an output that is capable of providing suitable energy to charge an energy storage module (during an interval between each light pulse produced by the flash lamp). The energy storage module is coupled to the output of the power supply module, and arranged to collect and store energy supplied by the power supply module to enable the flash lamp to be properly energized when triggered. The energy storage module, which is configured with an output having a characteristic impedance matched to the input impedance of the flash lamp, is structured to deliver a flattened and extended current pulse that is coupled to the energy input coupling of the flash lamp to energize the flash lamp in order to produce the high energy light pulse.

An optical system is further included to efficiently receive the light pulse produced by the flash lamp and deliver the light pulse to a selected hair follicle to effect the desired photo-thermal depilation of growth support tissue thereat. An optical light guide is provided having a first input end and a second output end. An optical coupler is structured to efficiently couple the light pulse produced by the flash lamp into the first input end of the optical light guide. The light pulse then travels along the optical light guide and is delivered to the second end (of the optical light guide). A tapered needle-less probe is provided at the second end of-the optical light guide and arranged to receive and deliver the light pulse to the selected hair follicle. The tapered probe is configured with an optical light guide portion structured to narrow and concentrate the light pulse before delivery to the growth support tissue of the selected hair follicle. The light pulse is narrowed and concentrated to provide a sufficient energy density to cause the desired photo-thermal coagulation.

A preferred embodiment of the energy storage module includes a charged delay line for energy storage and waveshaping purposes. When the flash lamp is-triggered, a current pulse is produced at the output of the energy storage module, and received by the flash lamp to produce the high energy light pulse. In a most preferred embodiment, the energy storage module includes a plurality of capacitors and a plurality of inductors arranged in a series-parallel configuration. The plurality of discrete inductors are arranged in a cascade, with each inductor having an input terminal and an output terminal. Each respective capacitor is connected between the output terminal of each inductor and a common reference (or return) node, thus forming the series-parallel configuration.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

PARTIAL LIST OF REFERENCE NUMERALS 10, 10a—photo-thermal epilation apparatus
14—(system) electronics module
15–flash lamp
16–flash lamp assembly
16a—energy input coupling (of flash lamp assembly 16)
16B—trigger terminal (of flash lamp assembly 16)
22—(flattened and extended) current pulse
26—power source
30—power supply module
30a—output of power supply 30
32—energy storage module
32a—output (of the energy storage module 32)
34—charged delay line
36—inductor
38—capacitor
42—optical coupler
46—optical light guide
46a—first end (of optical light guide 46)
46b—second end (of optical light guide 46)
60—(tapered needle-less) probe 60
60a—output end (of probe 60)
62—optical light guide portion
64—embedded computer (with user interface)
66—embedded controller module.
66a, 66b—operative links 66c—trigger signal
68—tube (of probe 60)
74—computer and user interface
88—detection means
90—calibration portal

DETAILED DESCRIPTION OF THE INVENTION

It is important to establish the definition of a number of terms that will be used throughout this disclosure. The term 'high energy light pulse' may be assumed to indicate a light pulse having a sufficient intensity (and or energy) level to effect photo-thermal depilation of growth support tissue of a selected hair follicle. Also, the terms 'high energy light pulse' and 'light pulse' may be assumed to be synonymous. The term 'sufficiently short duration', when applied to the duration of a suitable high energy light pulse, may be assumed to indicate a duration sufficiently short to prevent significant epidermal self-cooling, while causing the desired photo-thermal depilation. A number of other terms and definitions will be provided in the discussions that follow, as required, for a clear and complete understanding to the present invention.

Figure 1:
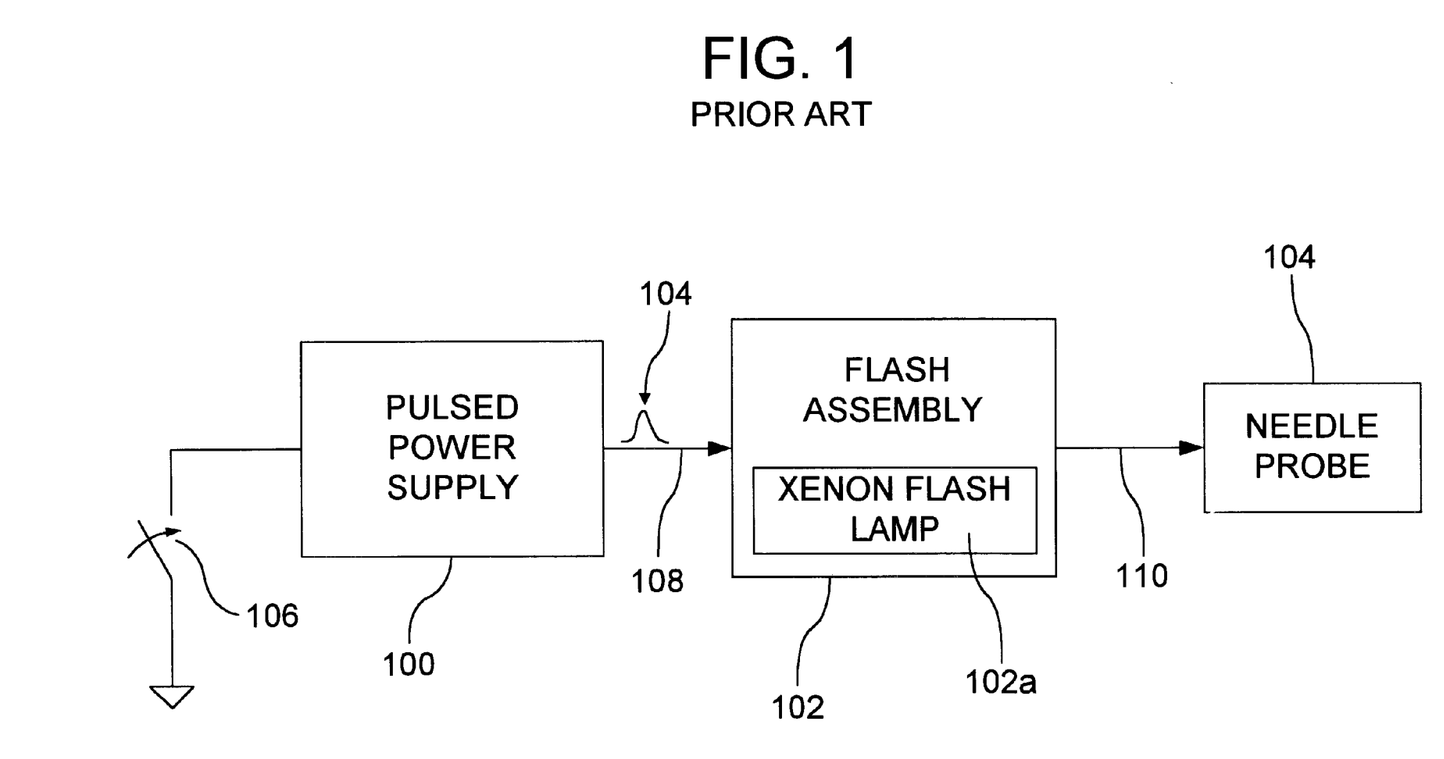
FIG. 1 depicts a typical prior art photo-thermal depilation system.

Referring now to FIG. 1, there is illustrated a portion of a prior art photo-depilation system. Included is a pulsed power supply 100, which is operatively coupled to a flash assembly 102 by an energy coupling 108. When triggered by an operator activated trigger switch 106, a xenon flash lamp 102a produces a high energy light pulse that may be delivered to a selected follicle by an optical coupling means 110 and (typically) a needle-type hollow tipped probe 104. As discussed above, the actual amount of energy reaching or delivered to the follicle is often a fraction of that produced by the xenon flash lamp 102a included in the flash assembly 102. Accordingly, a xenon flash lamp 102a would often be employed having a significantly higher power rating, and correspondingly higher maximum peak current to account for the inefficient optical portion of the prior art system.

The storage means employed to store the large amount of energy required to suitably energize the xenon flash lamp 102a in prior art systems is usually a large capacitor, or a bank of parallel capacitors. When the flash lamp 102a is triggered, the capacitor(s) are discharged into the energy coupling 108 of the flash lamp assembly 102, causing light output in the form of a high energy light pulse. If it was found that the light intensity or energy level produced was inadequate, then a larger gaussian shaped current pulse would be required.

Figure 2A:
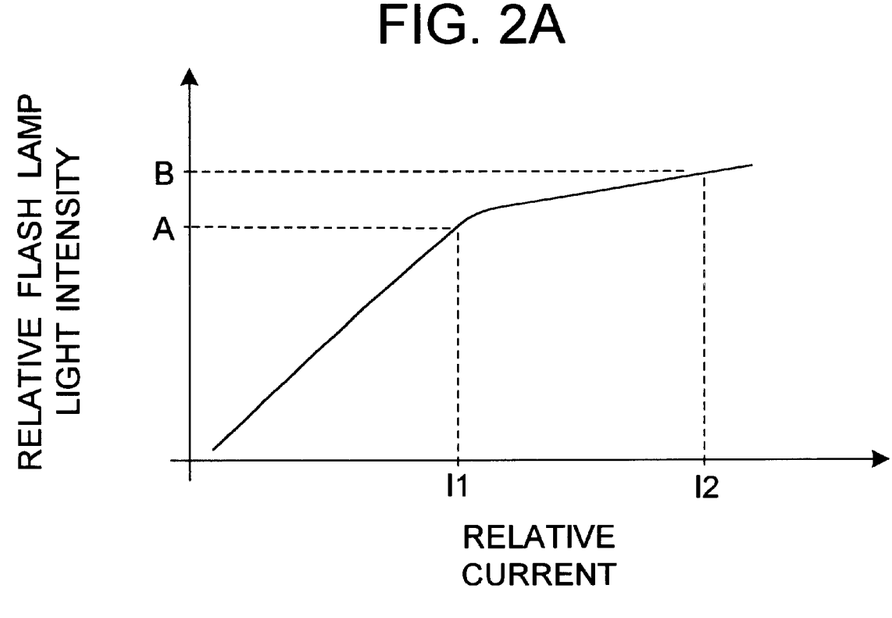
FIG. 2A provides a graph of relative light intensity produced by a xenon flash lamp with respect to the relative current employed to energize the flash lamp.

However, as understood by skilled persons, the light produced by a xenon flash lamp 102a is not linear after the current is increased above a certain level. An approximated piece-wise linear relationship for relative current versus relative flash lamp light intensity is provided in FIG. 2A. As can be seen in FIG. 2A, a linear relationship exists until the relative current applied to the flash lamp reaches a level I1. A corresponding relative light intensity or output level produced by a current level I1 may be assumed to be light intensity level A. Beyond this current level (i.e., beyond I1), a significant current increase is required to produce a modest increase in the light output. For example, as can be seen in FIG. 2A, a doubling of current from a level of I1 to a level of I2, produces a relatively small increase in the light intensity. In addition, the life expectancy of the flash lamp may be reduced considerably when operated at or near current level I2.

Figure 2B:
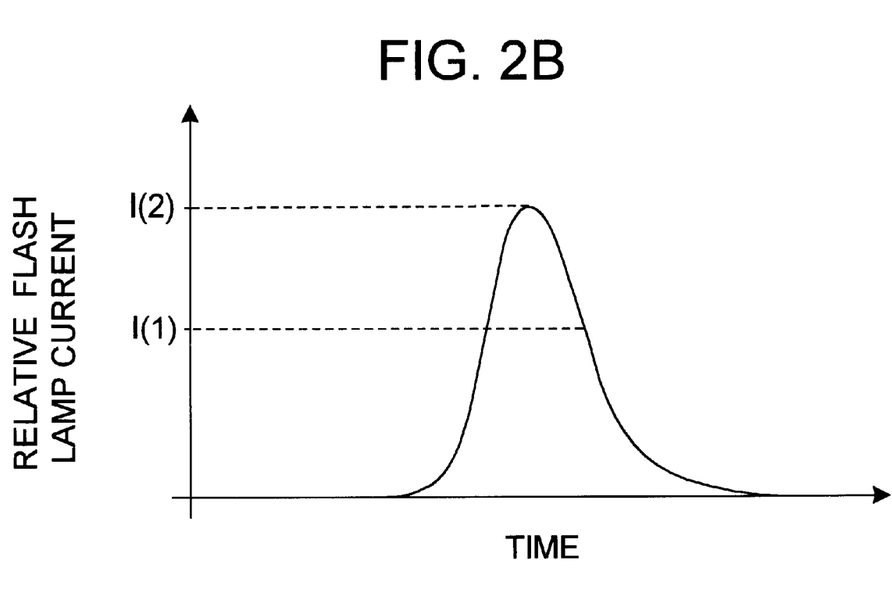
FIG. 2B depicts a current pulse as a function of time, which is typically employed to energize a flash lamp when triggered.
Figure 2C:
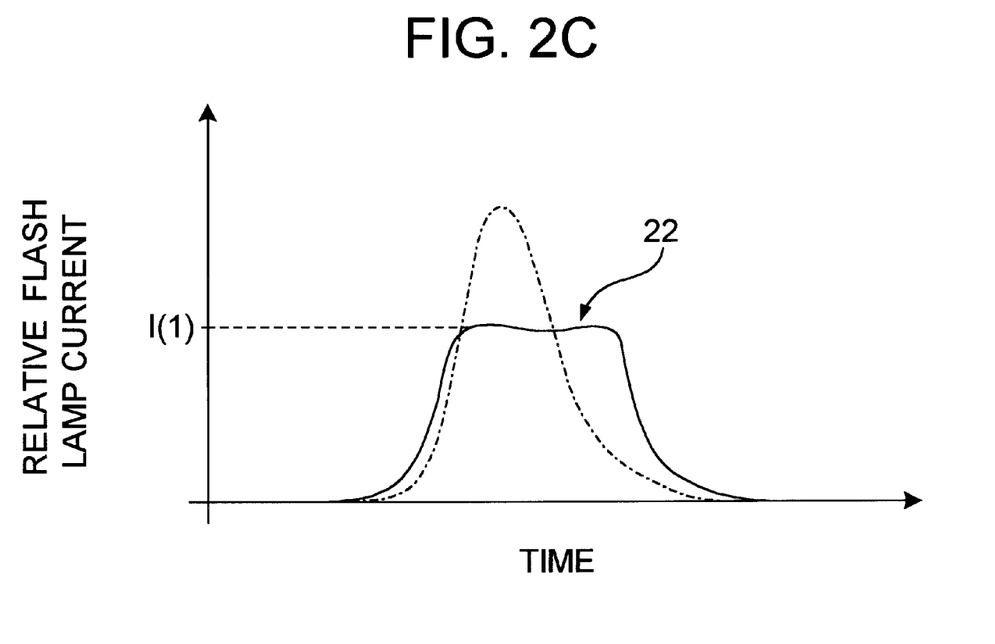
FIG. 2C shows a flattened and extended current pulse of the present invention that is coupled to energize a flash lamp to produce a high energy light pulse.

As can be seen in FIG. 2B, a typical current pulse that may be produced by coupling the energy stored by a simple capacitor based energy storage arrangement is gaussian in nature. As such, if I1 is assumed to be a safe and desired current level, but I2 is the current level that is required to produce the desired light intensity level, such a current pulse does not safely and efficiently energize the flash lamp. It would be most desirable to alter the energy storage arrangement to produce a current pulse that has a flattened and extended shape when coupled to energize the flash lamp. For example, the flattened and extended current pulse 22 depicted in FIG. 2C provides for the efficient energizing of a flash lamp (when energized by such a current pulse). The current pulse 22 of FIG. 2C enables an efficient current level be established and maintained for a suitable duration in order to produce a required high energy light pulse of the desired sufficiently short duration. Importantly, it has been determined that when a flash lamp is energized by a suitably flattened and extended current pulse, such as current pulse 22, a xenon flash lamp can be operated at a power level many times that of the power level recommended by the flash lamp manufacturer—with no apparent reduction in the operating life of the flash lamp. This unexpected result is essentially due to the reduction of the peak current to a lower and safer level.

Figure 3:
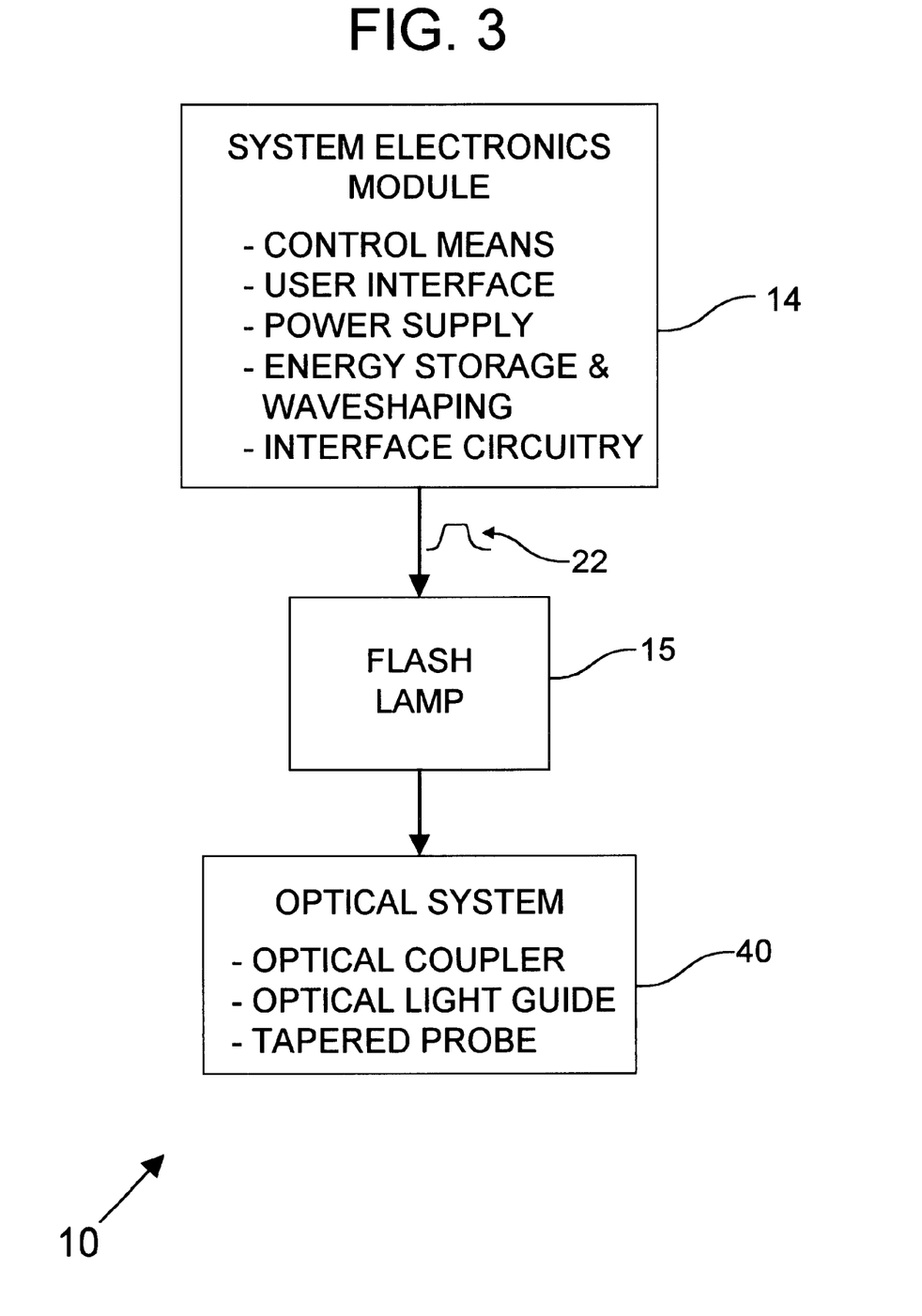
FIG. 3 illustrates a high level conceptual block diagram of an embodiment of the invention.

Turning now to FIG. 3, there is illustrated a high level conceptual block diagram of an embodiment of the photo-thermal epilation apparatus 10 of the present invention. A first major function block is provided by system electronics module 14. Electronics module 14 may be arranged to include a control means, and a user interface that is operatively coupled to the control means. Also provided is a power supply having an output capable of providing a suitable energy output. A preferred power supply or power supply module would have an output voltage of 500 to 700 volts, and an output current of approximately 10 to 20 milli-amperes. The energy provided by the power supply is collected and stored in an energy storage arrangement, included to enable the delivery of a flattened and extended current pulse to energize a flash lamp assembly (when a flash lamp 15 therein is triggered). In preferred embodiments the flattened and extended current pulse 22 may be have a maximum instantaneous current level of approximately 2000 to 4000 amperes. The flash lamp 15 periodically produces a light pulse each time it is triggered. Each respective light pulse is coupled to an optical system 40 and delivered to effect photo-thermal depilation of growth support tissue of a selected hair follicle. Additional features and characteristics of several embodiments of the invention will be discussed when referring to FIGS. 4 and 5.

Figure 4:
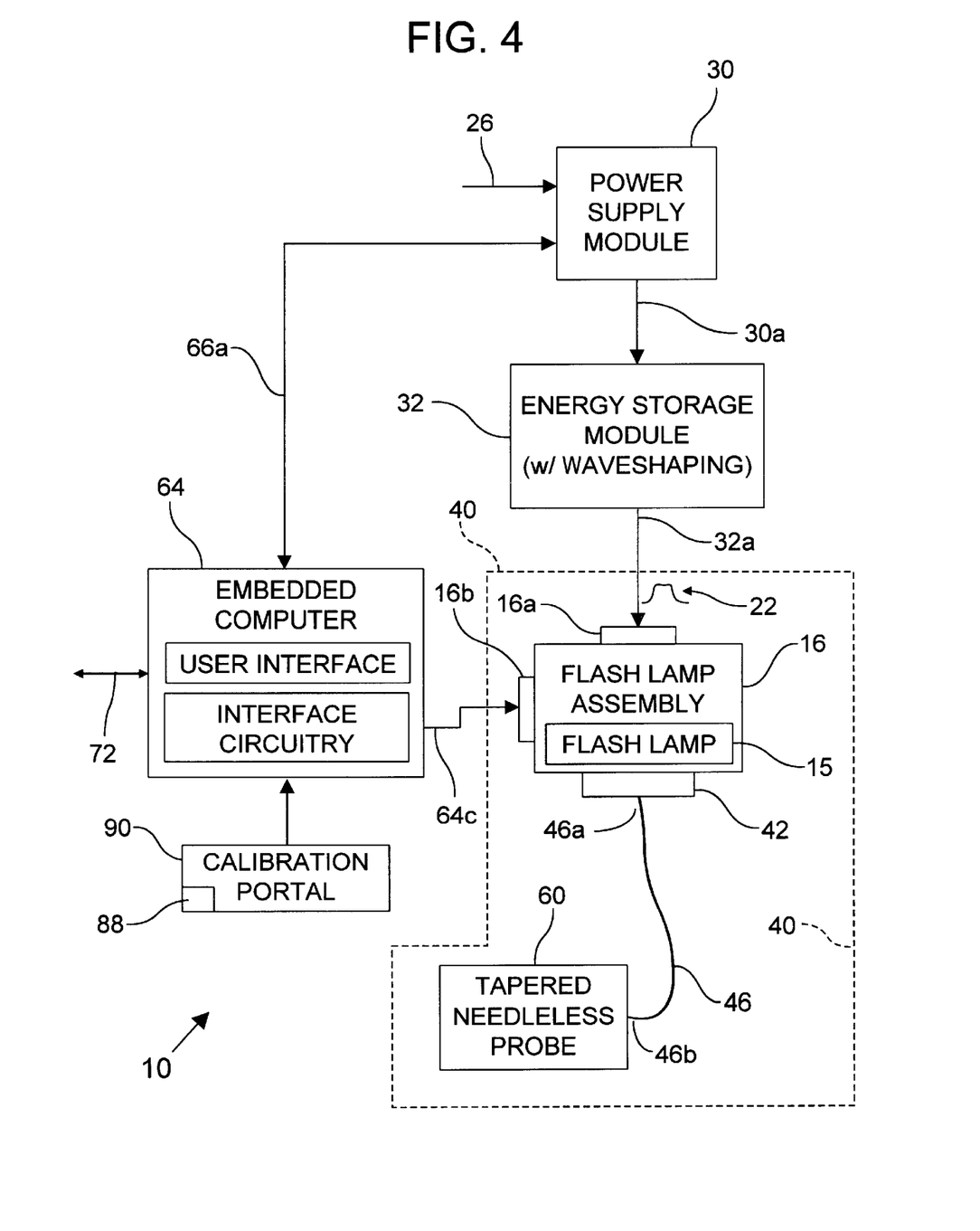
FIG. 4 provides a high level block diagram of a preferred embodiment of the invention.

Referring now to FIG. 4, there is provided a block diagram of a first preferred embodiment of a photo-thermal epilation apparatus 10 in accordance with the present invention. A power supply module 30 is included that is coupled to a power source 26. Power supply module 30 is configured with an output 30a that provides energy that is collected during an interval between each produced high energy light pulse. It should be noted that the power supply module 30 may continue to supply energy even as the light pulse is produced. However, the amount of energy produced during the short duration of the light pulse is quite small. The output 30a of the power supply 30 is coupled to an energy storage module 32, which is provided to collect and store sufficient energy. The energy collected and stored is coupled to an energy input coupling 16a of a flash lamp assembly 16, to properly energize the flash lamp 15 when triggered. The energy storage module 32 has an output 32a configured with a characteristic network impedance, which may be termed Z(network), that is importantly matched to the impedance (Zin) of the flash lamp assembly 16. As such, the output 32*a* of the energy storage module 32 is matched to the flash lamp 15 of the flash lamp assembly 16. This matched arrangement enables the efficient delivery of a flattened and extended current pulse 22 that is coupled from the output 32*a* (of the energy storage module) to the energy input coupling 16*a* to energize the flash lamp 15 to produce the desired high energy light pulse. It is important to recall that the high energy light pulse, having a sufficiently short duration, must be efficiently delivered to the growth support tissue of a selected hair follicle to effect photo-thermal depilation by way of a photo-coagulation process. A preferred duration of the light pulse would be less than 20 micro-seconds, with a most preferred duration being between 10 and 15 micro-seconds.

To enable the high energy light pulse to be suitably delivered to a selected follicle, the light pulse produced by the flash lamp assembly 16 (or more accurately the flash lamp 15) is delivered to the follicle by the optical system 40. The optical system 40 may be assumed to include the flash lamp assembly 16, an optical coupler 42, and a means to efficiently deliver the energy of the light pulse to the follicle. The optical coupler 42 is therefore structured to 'efficiently' (i.e., with minimum losses) couple the light pulse into a first (input) end 46*a* of an optical light guide 46. The optical light guide 46 is structured to cause the delivery of the light pulse, with minimal losses, to a second end 4*b* of the light guide 46. It may be noted that the term 'efficiently' may be assumed to be a relative term indicating that a reasonable amount of the light energy associated with the light pulse produced by the flash lamp assembly , say in the range of 20% to 50%, is coupled into the optical light guide 46 at the first end 46*a*. The optical light guide 46 may be provided by any suitable standard optical fiber or liquid core optical fiber. In a most preferred embodiment, light guide 46 is provided with a nominal diameter of 2 to 4 milli-meters. As can be seen in FIGS. 4, 5, 7A and 7B, a tapered needle-less probe 60 is provided at the second, end 46*b* of the optical light guide 46. The probe 60 is arranged to receive the light pulse coupled into the first end of the light guide 46 to effect the desired delivery of the light pulse to a selected hair follicle. Preferred diameters and configurations of the needle-less probe 60, will be fully discussed when referring to FIGS. 7A and 7B.

The embodiment of FIG. 4 may further include an embedded computer 64 (having a user interface), which may be very generally termed a 'control means'. The embedded computer 64 is provided to control the operation of the photo-thermal epilation apparatus 10 and support or enable a number of functional and or operational characteristics. For example, as can be seen in FIG. 4, the embedded computer 64 is arranged to periodically trigger the flash lamp assembly via an operative link 64*c* coupled to the trigger terminal 16*b*. Also, an operative link 66*a* may be employed to vary, say, the output voltage level of the power supply module 30.

Continuing with FIG. 4, it is contemplated that the trigger terminal 16*b* would be employed to trigger the flash lamp 15 of the flash lamp assembly 16 at a pre-determined rate (say once every second) for a pre-determined length of time (say 15 or 30 minutes). Such a 'length of time' may also be termed a 'session'. During the session a series of light pulses may be produced in spaced temporal succession. Each, light pulse is coupled into the optical light guide 46 and delivered via the probe 60 to a selected hair follicle to cause the desired photo-coagulation of the growth support tissue thereat. If the skill of an operator is somewhat low, the length of the interval between light pulses may be increased, using the user interface of the embedded computer 64. For example, while an operator is being trained, it may be preferable to produce a light pulse every 2 seconds, rather than a possibly most preferred 1 second interval. It is further contemplated that a user or operator may employ the user interface (of the embedded computer 64) to input other settings and information, as well as start, pause, and terminate a photo-thermal depilation session.

As would be appreciated by skilled persons, the embedded computer 64 may be provided in many varying forms. For example, standard microcontroller or microprocessor based designs are possible. Alternatively, commercially available single board computers may be employed. In addition, the user interface (not illustrated) may be structured to include a keypad, momentary and maintained switches, and possibly a display unit. It is important to understand that any design approach, even possibly those based on custom ASIC devices, that provides the required functionality is contemplated as being within the scope of the 'control means' of the present invention.

Figure 5:
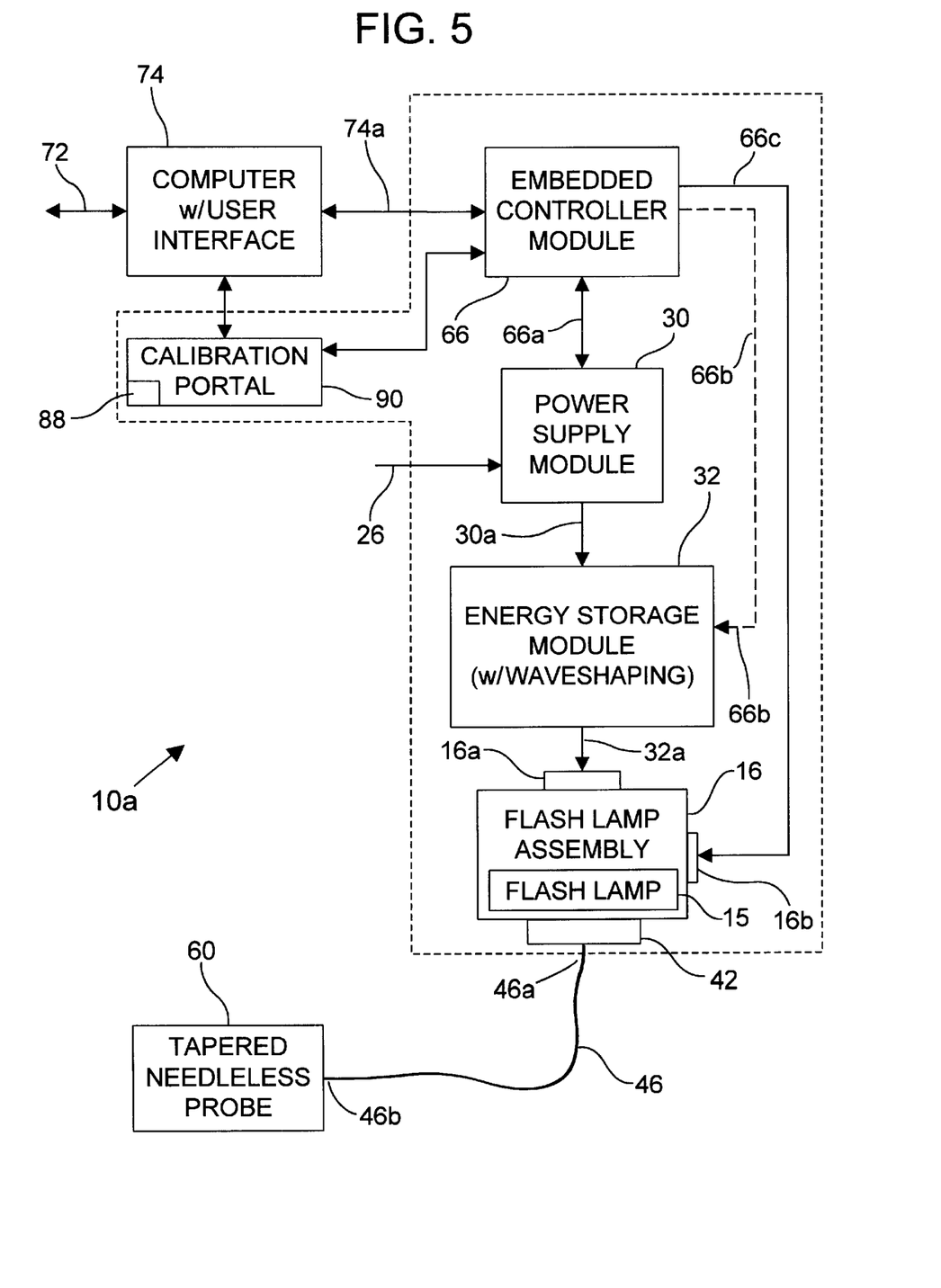
FIG. 5 provides a high level block diagram of another preferred embodiment of the present invention.

Another important feature of the present invention, which may be provided with the embodiments of FIG. 4 or FIG. 5, enables an operator to calibrate the amount of energy delivered to an output end 60*a* (see FIGS. 7A and 7B) of the probe 60 with each light pulse produced by the flash lamp 15. Accordingly, a calibration portal 90 may be included and structured to accept the output end 60*a* of the probe 60 to receive a precise sample (or known portion) of the light pulse energy delivered to said output end 60*a*. The term 'precise sample' is to be defined as a known portion of the light pulse energy, which is employed to enable calibration of the light pulse intensity to a desired pre-determined. intensity level. As such, this feature will enable an operator to periodically calibrate the photo-thermal depilation apparatus 10 to compensate for a number of phenomenon including the aging of the flash lamp 15 the 'drifting' of system modules or electronics, say over time or due to ambient temperature changes, etc. The calibration portal 90 may be embodied to include one or more known off-the-shelf photo-sensitive devices. One preferred device that may be included is a PIN diode (not shown), which would typically be structured with an optical window. Others photo-sensitive devices, as well as required signal conditioning circuitry needed to embody the calibration portal 90, may be provided by skilled persons.

Figure 7A:
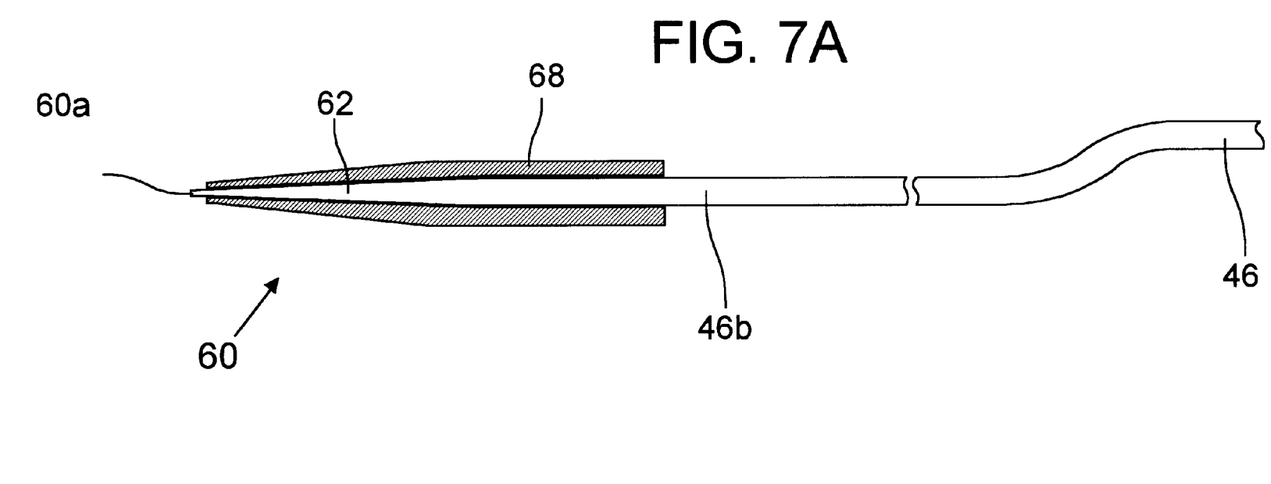
FIG. 7 depicts several embodiments of tapered (needle-less) probes in accordance with the present invention.
Figure 7B:
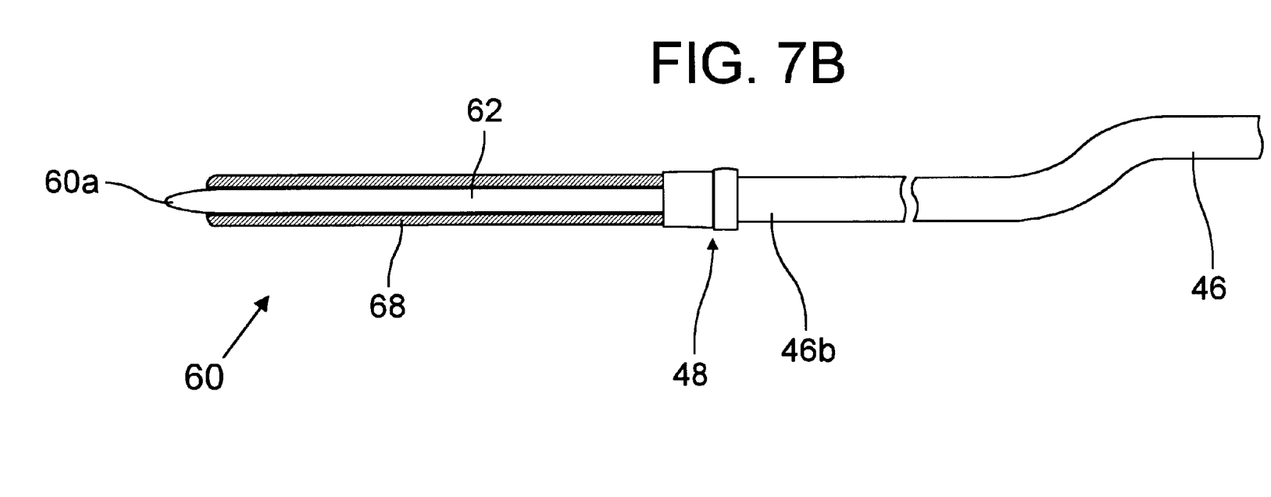

It may be noted that a preferred light pulse intensity level emitted from the output end 60*a* of the probe 60 is contemplated to be in the range of 1 to 20 joules per square centimeter, applied over an area having approximately a 0.5 milli-meter diameter. A most preferred light pulse intensity level is approximately 10 joules per square centimeter applied over an approximate area having the 0.5 milli-meter diameter). The term '0.5 milli-meter diameter', when discussing the area to which the light pulse is applied, is used for convenience due to the cross-sectional circular nature of the optical light guide 62. If should further be understood that the diameter is termed 'approximately 0.5 milli-meters' due to manufacturing tolerances, which may be in the range of 5% to 10%.

Turning now to FIG. 5, there is provided another preferred embodiment of the photo-thermal epilation apparatus 10*a* of the present invention. As with the embodiment of FIG. 4, a power supply module 30, a flash lamp assembly 16 (including flash lamp 15), an optical coupler 42, an optical light guide 46, and a probe 60 are again included. These items function in a manner essentially equivalent to the embodiment of FIG. 4. However, the embodiment of FIG. 5 is structured with an embedded controller 66 and an external computer 74 (providing a user interface). For example, the computer 74 may most preferably be provided by a lap-top type portable computer or a desktop personal computer. Accordingly, the computer 74 is contemplated to include a keyboard and display (not explicitly shown) that enables an operator to input and verify operational and other system/client information. Such information may include billing and or credit data, calibration and or maintenance information, client data, operator guidance, assistance, or training information, etc. Clearly, this arrangement enables a user to establish the pre-determined rate to periodically trigger the flash lamp 15 and or select the length of the time for a depilation session. As such, a portion of the information provided to the computer 74, may be supplied to or provided (as necessary) to the embedded controller module 66 by way of operative link 74a. In a preferred embodiment, operative link 74a would be provided by a simple serial communication channel. In a most preferred embodiment link 74a may be realized by a common RS-232C serial channel.

The embodiment of FIG. 5 may be structured with one or more operative links, such as links 66a and 66b, provided between the embedded controller module 66 and at least one of the power supply 30 and the energy storage module 32. Operative link 66a would most preferably be arranged to enable the control and adjustment of the energy level (or intensity) of the light pulse produced by the flash lamp 15. For example, link 66a may be arranged to enable the light pulse intensity to be suitably adjusted during calibration activities. Specifically, the level of an output voltage coupled to the energy storage module 32 may be suitably adjusted via link 66a, 66b, or other equivalent means, to enable the intensity of the high energy light pulse produced by the flash lamp 15 to be set to a desired level. In order to properly calibrate the intensity or energy level of the light pulse produced by the flash lamp 15, the calibration portal 90 would be employed as discussed above. As skilled persons would appreciate, during calibration of the photodepilation apparatus 10 and 10a, it would be desirable to verify when the output end 60a of the probe 60 is properly inserted into the calibration portal 90. Accordingly, a detection means 88 may be included to determine when the probe 60 is properly inserted and situated within the calibration portal 90, and the precise sample may be properly measured. The 'detection means' may be provided by a number of simple arrangements including one or more micro-switches, optical sensors, magnetic sensors, etc. As such, it is contemplated that the detection means 88 may be provided by any structure that enables a determination of when the output end 60a of the probe 60 is properly inserted into the calibration portal 90.

The embodiment of FIG. 5 may also include an communication channel 72 provided to enable the photo-thermal epilation apparatus 10a to be linked via a communication network to a remote system (not shown). The linking to the remote system may be employed for a variety of reasons including billing purposes, remote monitoring considerations, updating of system operating software, user training and evaluation, insuring safe and reliable operating procedures, security, etc. It may be noted that the interface to communication channel 72 may be provided by a modem, network interface card, a wireless link, an optical link,.or other known communication supporting arrangements that may be provided with computer 74.

Figure 6:
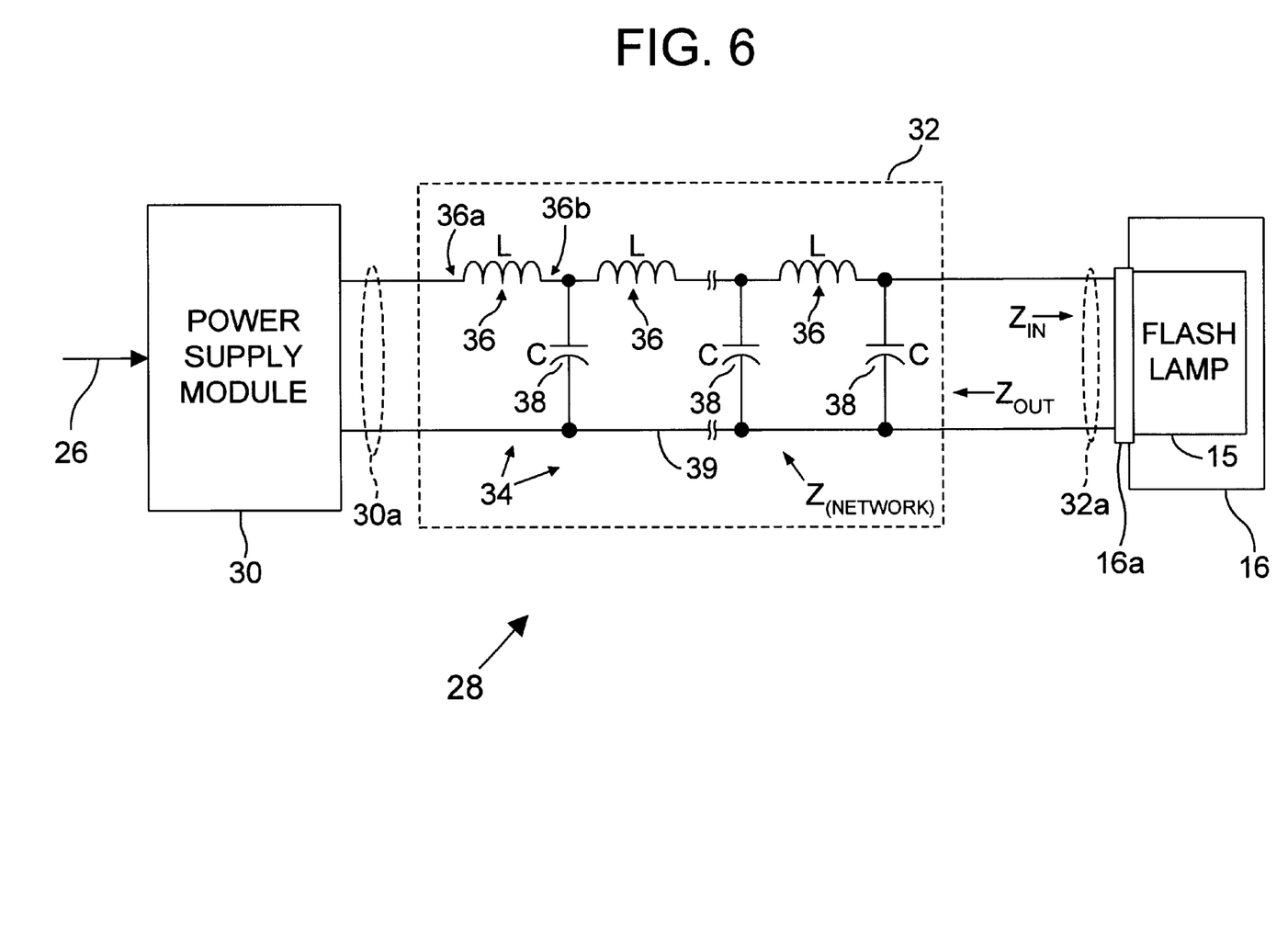
FIG. 6 shows a most preferred embodiment of an energy storage module, including a 'waveshaping' capability, to produce a flattened and extended current pulse that is coupled to energize a flash lamp.

Turning now to FIG. 6, a preferred embodiment of an energy supplying arrangement 28 is illustrated. The energy supplying arrangement 28 may be assumed to include the power supply module 30, along with the energy storage module 32. In a preferred embodiment of the energy storage module 32, a charged delay line 34 is employed to provide energy storage and waveshaping to enable the desired flattened and extended current pulse 22 to be produced. The current pulse is flattened to limit the peak current to a level equal to or less than a recommended maximum current level specified, for example, by the manufacturer of the flash lamp 15. As such, it may be assumed that the current pulse is flattened so as to not exceed the maximum recommended current level, and additionally is extended to fully energize the flash lamp 15 when triggered to produce a high energy light pulse of a desired intensity level—even with the peak current limited.

As can be seen in FIG. 6, a preferred embodiment of the charged delay line 34 of the energy storage module 32 is structured with a plurality of capacitors 38 and a plurality of inductors 36. As clearly shown, the inductors 36 and capacitors 38 are arranged in what may be termed a 'series-parallel configuration'. Accordingly, the plurality of inductors 36 shown in FIG. 6 are arranged in a cascade, with each inductor 36 having an input terminal 36a and an output terminal 36b. Each respective capacitor 38 is connected between a respective output terminal 36b of each inductor 36 and a common reference (or return) node 39, thus forming the series-parallel configuration. Although the embodiment of the charged delay line 34 is depicted in FIG. 6 as having 3 sections (with each section formed by one inductor 36 and one capacitor 38), any suitable number of sections may be employed, as required to produce a desired flattened and extended current pulse.

An important characteristic of the energy storage module 32 of FIGS. 4, 5, and 6, is that its output impedance Zout, which is determined by a network impedance Z(network) of the energy storage module 32, is matched to the impedance of the flash lamp 15. The value of Z(network) may be assumed to be approximately equal to the square root of the ratio of the inductance L of inductor 36 and the capacitance C of capacitor 38. Therefore, Z(network) may be defined by the formula: $Z(network)=(L/C)^{1/2}$. Further, the pulse width of the flattened and extended current pulse is equal to 2 times the square root of the product of the total inductance and the total capacitance of the charged delay line 34. Therefore, the length or duration of-the pulse width may be calculated by using the formula:

$$PW\ Duration = 2 \times [L(total) \times C(total)]^{1/2}$$

As will be appreciated by skilled persons, other equivalent arrangements may be provided to embody the energy storage module 32 and the charged delay line 34 in accordance with the invention. Accordingly, the embodiment of FIG. 6 is illustrative of a preferred embodiment.

In summary, it is important to understand that a fundamental method of the embodiments of present invention, including the embodiments of FIG. 4 and FIG. 5, may be described as follows. In order to properly energize a (triggered) flash lamp 15 to produce a high energy-light pulse of a sufficiently short duration, a first step involves the collecting and storing of energy provided at the output 30a of the power supply module 30. Subsequently, the stored energy is delivered to the flash lamp 15 (of the flash lamp assembly 16) in the form of a flattened and extended current pulse coupled to energize the flash lamp 15. The flattened and extended current pulse is provided by, or coupled from, the output 32a of an energy storage module 32 in order to properly energize the flash lamp 15 to produce the required high energy light pulse, a portion of which is ultimately delivered to a selected follicle.

Referring now to FIGS. 7A and 7B, there is illustrated therein several embodiments of tapered (needle-less) probes in accordance with the present invention. As can be seen, a tapered needle-less probe 60 is provided at the second end 46b of the optical light guide 46. The probe 60 is arranged to receive the high energy light pulse coupled into the first end 46a of the light guide 46 to effect the delivery of the light pulse (emitted from the output end 60a) to the hair follicle. Importantly, the probe 60 is configured with an optical light guide portion 62 structured at a distal end to narrow and concentrate the light pulse delivered to the growth support tissue of the hair follicle. The narrowed and concentrated light pulse, as applied to the surface of the epidermis, will preferably have an approximate diameter of 0.3 to 0.7 milli-meters. A most preferable diameter will be approximately 0.5 milli-meters.

As can be clearly seen in FIGS. 7A and 7B, a tube 68 may be provided that is coextensively disposed over the optical light guide portion 62. The tube 68 may further include a suitable friction enhancing arrangement, such as knurling or a rubber coating, to enable easy and sure grasping by an operator during calibration and treatment activities. It is further contemplated that the probe 60 may be constructed with the optical light guide portion 62 being provided by an end portion of a single optical light guide 46 as shown in FIG. 7A. Alternately, an optical coupler 48 may be included to couple the probe 60 (including optical light guide portion 62) to the second end 46b of the light guide 46, as illustrated in FIG. 7B.

While there have been described a plurality of the currently preferred embodiments of the present invention, along with varied methods of operation, those skilled in the art will recognize that other and further modifications may be made without departing from the invention and it is intended to claim all modifications and variations as fall within the scope of the invention and the appended claims.

What is claimed is:

1. An energy supplying arrangement for use in energizing a trigger activated flash lamp to periodically produce a high energy light pulse of a sufficiently short duration to cause thermal-depilation when the energy supplying arrangement is employed in a photo-thermal epilation system wherein the light pulse is suitably delivered to the growth support tissue of a selected hair follicle, the energy supplying arrangement comprising:
   (a) a power supply module having an output capable of providing suitable energy during an interval between the production of a respective light pulse; and
   (b) an energy storage module coupled to the output of the power supply module to store energy supplied thereby, the energy storage module having an output with a characteristic impedance substantially matched to an input impedance of the flash lamp, the energy storage module structured to deliver a flattened and extended current pulse coupled from the output of the energy storage module to an energy input coupling to energize the flash lamp in order to produce the high energy light pulse when the flash lamp is triggered.

2. The energy supplying arrangement according to claim 1, wherein the energy storage module includes a charged delay line which provides energy storage and waveshaping to produce the flattened and extended current pulse.

3. The energy supplying arrangement according to claim 2, wherein the charged delay line includes a plurality of cascaded discrete inductors and a plurality of discrete capacitors connected between at an output terminal of each respective inductor and a common reference node.

4. In an improved photo-thermal epilation apparatus employed to effect permanent hair removal by delivering a high energy light pulse produced by a flash lamp having an energy input coupling and a trigger terminal, the light pulse having a sufficiently short duration, and delivered via an optical coupler and an optical light guide to effect photo-thermal depilation of growth support tissue of a selected single hair follicle, wherein the improvement comprises:
   (a) an energy storage module coupled to a power supply module to store energy supplied thereby, the energy storage module having an output with a characteristic impedance matched to an input impedance of the flash lamp when triggered, the energy storage module structured to support the periodic delivery of a flattened and extended current pulse that is coupled from the is energy storage module to the energy input coupling of the flash lamp to energize the flash lamp in order to produce the high energy light pulse when the flash lamp is triggered by way of the trigger terminal; and
   (b) a tapered needle-less probe provided at a second end of the optical light guide and arranged to receive, narrow, and concentrate the light pulse to effect delivery of the light pulse to the hair follicle to cause the desired photo-thermal depilation of the growth support tissue thereat.

5. The photo-thermal epilation apparatus according to claim 4, wherein the energy storage module includes a charged delay line structured with a plurality of capacitors and a plurality of inductors arranged in a series-parallel configuration to provide energy storage and waveshaping as required to produce the flattened and extended current pulse.

6. The photo-thermal epilation apparatus according to claim 5, wherein the current pulse is suitably flattened to produce a peak current equal to or less than a recommended maximum current level that may be coupled to the energy input coupling of the flash lamp, the pulse additionally extended to fully energize the flash lamp when triggered to produce a light pulse of a desired intensity, even with a limited peak current.

7. A photo-thermal epilation apparatus employable to effect permanent hair removal by delivering a high energy light pulse of a sufficiently short duration to effect photo-thermal depilation of growth support tissue of a selected hair follicle, the photo epilation apparatus comprising:
   (a) a flash lamp having an energy input coupling and a trigger terminal;
   (b) a power supply module having an output capable of providing suitable energy during an interval between light pulses;
   (c) an energy storage module coupled to the output of the power supply module to collect and store energy supplied thereby, the energy storage module having an output with a characteristic impedance matched to an input impedance of the flash lamp, the energy storage module structured to deliver a flattened and extended current pulse coupled from the output of the energy storage module to the energy input coupling to energize the flash lamp in order to produce the high energy light pulse when the flash lamp is triggered;
   (d) an optical light guide having a first end and a second end;
   (e) an optical coupler structured to efficiently couple the light pulse produced by the flash lamp into the first end of the optical light guide causing the delivery of the light pulse to the second end thereof; and (f) a needle-less probe provided at the second end of the optical light guide and arranged to receive the light pulse to effect the efficient delivery of the light pulse to the hair follicle causing the photo-thermal depilation of the growth support tissue thereat;

(g) the probe configured with an optical light guide portion structured to narrow and concentrate the light pulse delivered to the growth support tissue of the hair follicle.

8. The photo-thermal epilation apparatus according to claim 7, wherein the energy storage module includes a charged delay line for energy storage and waveshaping of the current pulse produced at the output of the energy storage module and delivered to the flash lamp when triggered.

9. The photo-thermal epilation apparatus according to claim 8, further including a control means to trigger the flash lamp at a pre-determined rate for a pre-determined length of time to produce a series of light pulses, each light pulse coupled into the optical light guide and delivered via the probe to effect photo-thermal depilation of growth support tissue of a selected hair follicle.

10. The photo-thermal epilation apparatus according to claim 9, wherein the control means is provided by an embedded computer having a user interface, the user interface enabling an operator to configure and conduct a session during which the photo-thermal depilation of growth support tissue of a succession of selected single hair follicles is achieved.

11. The photo-thermal epilation apparatus according to claim 10, wherein the length of the session may be established by the operator using the user interface.

12. The photo-thermal epilation apparatus according to claim 10, wherein the embedded computer is configured to adjust an output level of the power supply module to establish a desired light pulse intensity produced with each triggering of the flash lamp.

13. The photo-thermal epilation apparatus according to claim 12, further including a calibration portal structured to accept an output end of the probe to receive a precise sample of the light pulse delivered to the output end to enable calibration of the light pulse intensity to a desired level.

14. The photo-thermal epilation apparatus according to claim 13, wherein the calibration portal includes a detection means to determine when the probe has been suitably located within the portal to enable the precise sample to be properly measured.

15. The photo-thermal epilation apparatus according to claim 7, wherein a duration of the light pulse produced is less than 20 micro-seconds.

16. The photo-thermal epilation apparatus according to claim 15, wherein the light pulse intensity emitted from an output end of the probe is in the range of 1 to 20 joules per square centimeter applied over an area having approximately a 0.5 milli-meter diameter.

17. The photo-thermal epilation apparatus according to claim 16, wherein the light pulse intensity emitted from the output end of the probe is approximately 10 joules per square centimeter.

18. The photo-thermal epilation apparatus according to claim 16, wherein the probe is structured having a taper provided proximate to an output end of the probe.

* * * * *

UNITED STATES PATENT AND TRADEMARK OFFICE
CERTIFICATE OF CORRECTION

PATENT NO.    : 6,461,348 B1
DATED         : October 8, 2002
INVENTOR(S)   : Bertan et al.

It is certified that error appears in the above-identified patent and that said Letters Patent is hereby corrected as shown below:

<u>Title page,</u>
ABSTRACT,
Line 7, after "storage", delete the period (.).
At the end of line 10, following "in order to", delete "the".

<u>Column 3,</u>
Line 52, after "of" and before "the optical light guide", delete the hyphen (-).

<u>Column 12,</u>
Line 18, after "coupled from the", delete "is".

Signed and Sealed this

Fourth Day of March, 2003

JAMES E. ROGAN
*Director of the United States Patent and Trademark Office*